(12) United States Patent
Wataya

(10) Patent No.: US 11,717,138 B2
(45) Date of Patent: Aug. 8, 2023

(54) IMAGING UNIT, ENDOSCOPE AND ENDOSCOPE SYSTEM HAVING OPTICAL SYSTEMS WITH OVERLAPPING DEPTH OF FIELDS

(71) Applicant: OLYMPUS CORPORATION, Tokyo (JP)

(72) Inventor: Yuichi Wataya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 431 days.

(21) Appl. No.: 17/152,118

(22) Filed: Jan. 19, 2021

(65) Prior Publication Data

US 2021/0137359 A1   May 13, 2021

Related U.S. Application Data

(63) Continuation of application No. PCT/JP2019/009195, filed on Mar. 7, 2019.

(30) Foreign Application Priority Data

Jul. 20, 2018   (JP) .................. 2018-136697

(51) Int. Cl.
*A61B 1/00*   (2006.01)
*A61B 1/05*   (2006.01)

(52) U.S. Cl.
CPC .... *A61B 1/000095* (2022.02); *A61B 1/00096* (2013.01); *A61B 1/000096* (2022.02);
(Continued)

(58) Field of Classification Search
CPC .................................................. G02B 23/2415
See application file for complete search history.

(56) References Cited

U.S. PATENT DOCUMENTS 5,743,847 A   4/1998 Nakamura et al.
2012/0133739 A1   5/2012 Morimitsu
(Continued)

FOREIGN PATENT DOCUMENTS

CN   103875243 A   *   6/2014   ......... A61B 1/00009
JP   H8-194170 A       7/1996
(Continued)

OTHER PUBLICATIONS

International Search Report dated May 21, 2019 issued in PCT/JP2019/009195.

*Primary Examiner* — John P Leubecker
(74) *Attorney, Agent, or Firm* — Scully, Scott, Murphy & Presser, P.C.

(57) ABSTRACT

An imaging unit includes: a first lens group configured to form a first optical image; a second lens group configured to form a second optical image; an objective lens group having a first region and a second region; a single image sensor configured to generate an image signal; a first holding frame having a first holding hole and a second holding hole; a second holding frame configured to hold the objective lens group; and a third holding frame configured to hold the image sensor. A depth of field of a first optical system formed of the objective lens group and the first lens group is set so as to entirely include a depth of field of a second optical system formed of the objective lens group and the second lens group and to be deeper than the depth of field of the second optical system.

4 Claims, 4 Drawing Sheets

(52) U.S. Cl.
CPC ...... *A61B 1/00147* (2013.01); *A61B 1/00163* (2013.01); *A61B 1/00193* (2013.01); *A61B 1/05* (2013.01); *A61B 1/00188* (2013.01)

(56) References Cited

U.S. PATENT DOCUMENTS

| | | | |
|---|---|---|---|
| 2018/0045948 A1 | 2/2018 | Unsai et al. | |
| 2018/0077404 A1* | 3/2018 | Bechtel | H04N 13/296 |
| 2018/0295265 A1 | 10/2018 | Suga | |
| 2019/0102900 A1* | 4/2019 | Uchida | G06T 7/593 |

FOREIGN PATENT DOCUMENTS

| | | |
|---|---|---|
| JP | H9-5643 A | 1/1997 |
| JP | 2003-60947 A | 2/2003 |
| JP | 2012-118698 A | 6/2012 |
| JP | 2018-40927 A | 3/2018 |
| WO | 2017/104191 A1 | 6/2017 |
| WO | 2017/104276 A1 | 6/2017 |
| WO | 2017/199666 A1 | 11/2017 |

\* cited by examiner

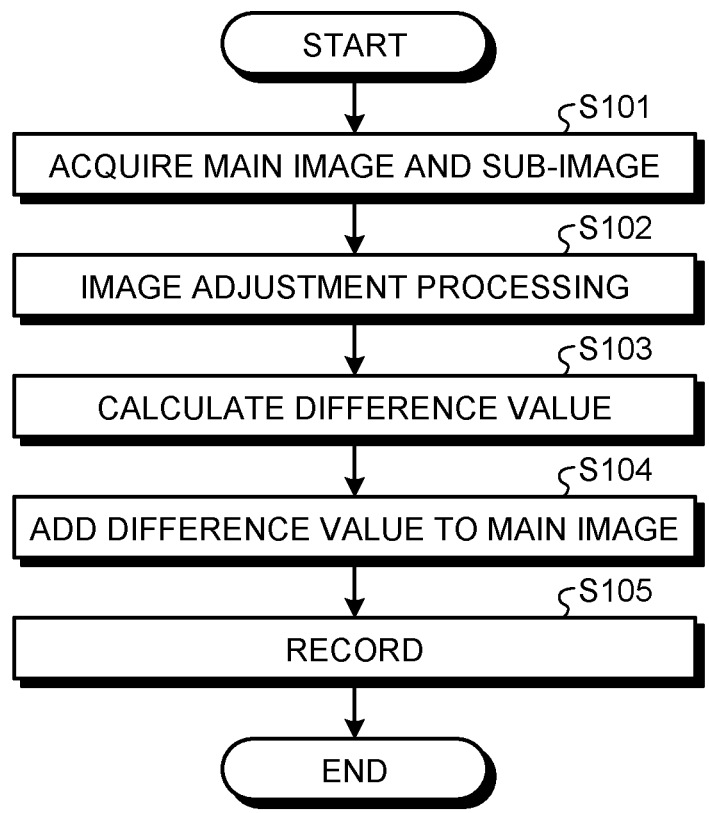

IMAGING UNIT, ENDOSCOPE AND ENDOSCOPE SYSTEM HAVING OPTICAL SYSTEMS WITH OVERLAPPING DEPTH OF FIELDS

CROSS-REFERENCE TO RELATED APPLICATIONS

This application is a continuation of PCT international application No. PCT/JP2019/009195 filed on Mar. 7, 2019, which designates the United States, incorporated herein by reference, and which claims the benefit of priority from Japanese Patent Application No. 2018-136697, filed on Jul. 20, 2018, incorporated herein by reference.

BACKGROUND

1. Technical Field

The present disclosure relates to an imaging unit provided at a distal end of an insertion portion of an endoscope inserted into a subject to capture an image of an inside of the subject, the endoscope, and an endoscope system.

2. Related Art

In the related art, a technique for an endoscope is known that observes a stereoscopic image (hereinafter, simply referred to as "3D image") inside a subject by forming two images with different parallaxes on an imaging surface of one image sensor (see International Publication No. 2017/104276). In this technique, by providing different holding frames for focus adjustment in a primary optical system and a secondary optical system that generate two optical images each having a parallax, a difference in focus positions of the primary optical system and the secondary optical system due to manufacturing errors is kept within a certain allowable range, and thus a 3D image is generated.

SUMMARY

In some embodiments, an imaging unit includes: a first lens group configured to form a first optical image; a second lens group configured to form a pair with the first lens group and form a second optical image; an objective lens group having a first region that guides object light to the first lens group and a second region that guides object light to the second lens group; a single image sensor configured to generate an image signal by receiving the first optical image and the second optical image;

a first holding frame having a first holding hole in which the first lens group is held and a second holding hole in which the second lens group is held; a second holding frame configured to hold the objective lens group, the second holding frame being positioned and fixed with respect to the first holding frame by being adhered to a distal end side of the first holding frame in a state where the second holding frame is fitted to the distal end side of the first holding frame; and a third holding frame configured to hold the image sensor, the third holding frame being positioned and fixed with respect to the first holding frame by being adhered to a proximal end side of the first holding frame in a state where the third holding frame is fitted to the proximal end side of the first holding frame on an inner peripheral surface of the third holding frame. A depth of field of a first optical system formed of the objective lens group and the first lens group is set so as to entirely include a depth of field of a second optical system formed of the objective lens group and the second lens group and to be deeper than the depth of field of the second optical system.

In some embodiments, an endoscope includes: an insertion portion to be inserted into a subject; an imaging unit provided on a distal end side of the insertion portion and generating an image signal by capturing an image of the subject; and a proximal end portion provided on a proximal end side of the insertion portion and detachably connected to a processor configured to perform image processing on the image signal. The imaging unit includes a first lens group configured to form a first optical image; a second lens group configured to form a pair with the first lens group and form a second optical image; an objective lens group having a first region that guides object light to the first lens group and a second region that guides object light to the second lens group; a single image sensor configured to generate an image signal by receiving the first optical image and the second optical image; a first holding frame having a first holding hole in which the first lens group is held and a second holding hole in which the second lens group is held; a second holding frame configured to hold the objective lens group, the second holding frame being positioned and fixed with respect to the first holding frame by being adhered to a distal end side of the first holding frame in a state where the second holding frame is fitted to the distal end side of the first holding frame; and a third holding frame configured to hold the image sensor, the third holding frame being positioned and fixed with respect to the first holding frame by being adhered to a proximal end side of the first holding frame in a state where the third holding frame is fitted to the proximal end side of the first holding frame on an inner peripheral surface of the third holding frame. A depth of field of a first optical system formed of the objective lens group and the first lens group is set so as to entirely include a depth of field of a second optical system formed of the objective lens group and the second lens group and to be deeper than the depth of field of the second optical system.

In some embodiments, an endoscope system includes: the endoscope according to claim 3; and a processor configured to acquire, based on the image signal, a first image generated by the first optical system and a second image generated by the second optical system, calculate a parallax value that is an amount of deviation of a predetermined position of each of the second image and the first image, calculate, based on the parallax value, a difference value between luminance information of each pixel of the second image and luminance information of each pixel of the first image, and add the difference value to a pixel value of each pixel of the second image.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 6 is a flowchart illustrating an outline of processing executed by the processing device according to one embodiment of the present disclosure.

DETAILED DESCRIPTION

Figure 1:
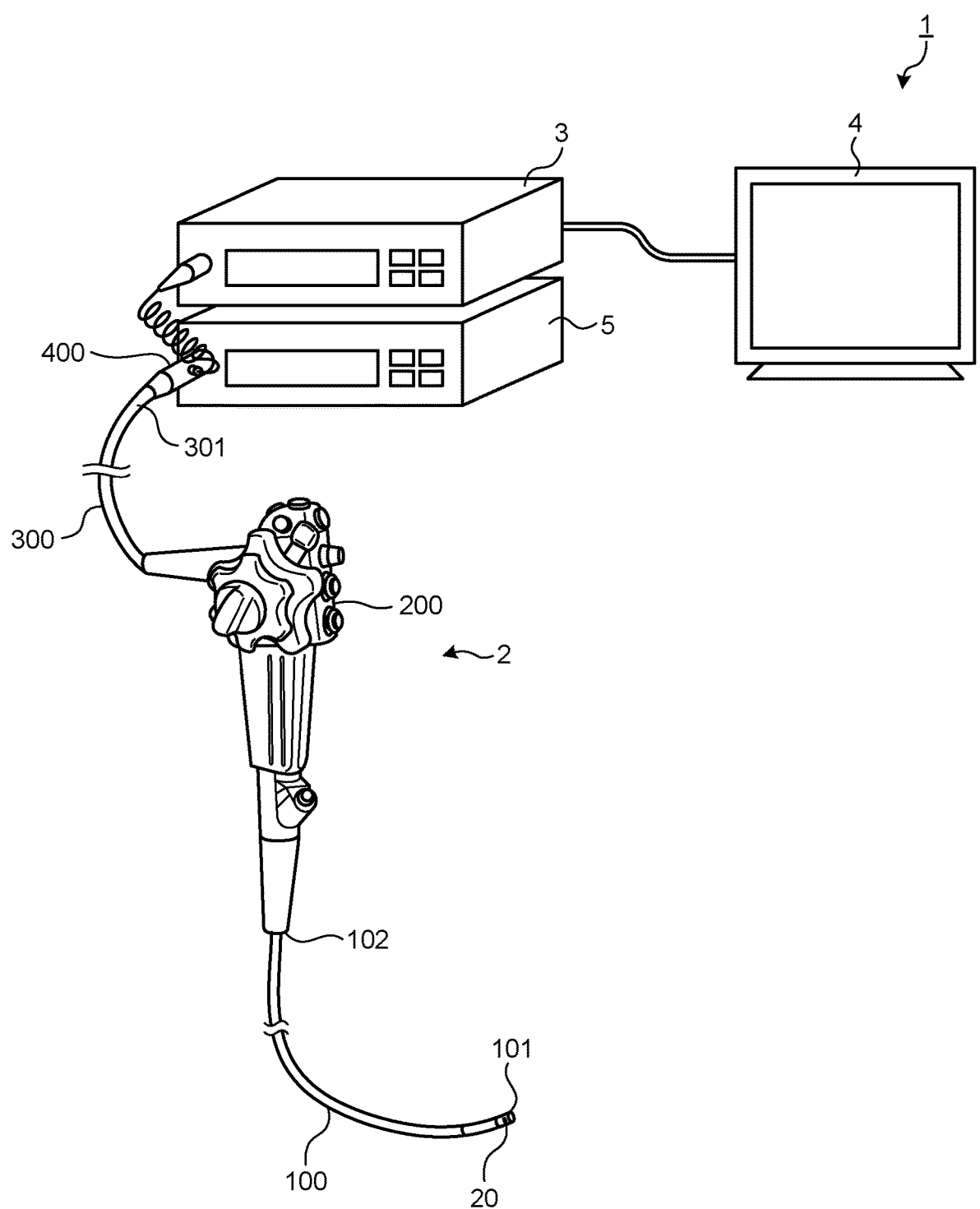
FIG. 1 is a schematic view schematically illustrating an overall configuration of an endoscope system according to one embodiment of the present disclosure.

Hereinafter, as a mode for carrying out the present disclosure (hereinafter, referred to as "embodiment"), an endoscope system will be described that is provided with an endoscope having an imaging unit (imaging device) at a distal end portion on a distal end side of an insertion portion to be inserted into a subject. Moreover, this embodiment does not limit the present disclosure. Further, in the description of the drawings, the same parts will be described with the same reference numerals. Furthermore, it should be noted that the drawings are schematic, and the relationship between the thickness and width of each member, the ratio of each member, and the like are different from the reality. In addition, parts of the drawings having different dimensions and ratios are included.

Configuration of Endoscope System

FIG. 1 is a schematic view schematically illustrating an overall configuration of an endoscope system according to one embodiment of the present disclosure. An endoscope system 1 illustrated in FIG. 1 includes an endoscope 2, a processing device 3, a display device 4, and a light source device 5.

The endoscope 2 outputs, to the processing device 3, an imaging signal generated by inserting an insertion portion 100 including a plurality of cables and a light guide into a body cavity of a subject, and capturing an image of an inside of the subject. The endoscope 2 includes an insertion portion 100, an operation unit 200, a universal cord 300, and a proximal end portion 400.

The insertion portion 100 has the plurality of cables and the light guide inside of the insertion portion 100, and is inserted into the body cavity of the subject. A distal end portion 101 of the insertion portion 100 is arranged on a distal end side to be inserted into the body cavity of the subject and is provided with an imaging unit 20 that generates an imaging signal by capturing an image of the inside of the subject. The operation unit 200 is connected to a proximal end side 102 of the insertion portion 100. The insertion portion 100 transmits power and a drive signal supplied from the processing device 3 to the imaging unit 20, and also transmits the imaging signal generated by the imaging unit 20 to the proximal end side 102.

The operation unit 200 has a built-in board on which various circuits are mounted, and receives inputs for various operations related to the endoscope 2. Further, the universal cord 300 is connected to the operation unit 200. The operation unit 200 is configured by using various switches, toggle switches, buttons, and the like.

The universal cord 300 has a plurality of cables and a light guide inside of the universal cord 300, and the proximal end portion 400 is connected to a proximal end side 301 of the universal cord 300. The universal cord 300 transmits the power and the drive signal supplied from the processing device 3 to the insertion portion 100 via the proximal end portion 400 and the operation unit 200, and also transmits the imaging signal generated by the imaging unit 20 to the proximal end portion 400 via the insertion portion 100 and the operation unit 200.

The proximal end portion 400 is detachably connected to the processing device 3 and the light source device 5. The proximal end portion 400 transmits the power and the drive signal supplied from the processing device 3 to the universal cord 300, and also transmits the imaging signal input via the universal cord 300 to the processing device 3.

The processing device 3 outputs the power and the drive signal to the proximal end portion 400, and receives the imaging signal input from the proximal end portion 400. The processing device 3 performs predetermined image processing on the imaging signal and outputs the imaging signal to the display device 4. The processing device 3 controls each unit of the endoscope system 1. The processing device 3 is configured by using, for example, a central processing unit (CPU), a graphics processing unit (GPU), a field programmable gate array (FPGA), a digital signal processing (DSP), a volatile memory, a non-volatile memory, and the like.

The display device 4 displays an image corresponding to the imaging signal subjected to image processing by the processing device 3. In addition, the display device 4 displays various information related to the endoscope system 1. The display device 4 is configured by using a liquid crystal, an organic electro luminescence (EL), or the like.

The light source device 5 supplies illumination light so as to irradiate the subject (subject) with the illumination light from a side of the distal end portion 101 of the insertion portion 100 via the proximal end portion 400. The light source device 5 is configured by using a halogen lamp, a white light emitting diode (LED) that emits white light, or the like. In the present embodiment, a case where a simultaneous lighting method is used for the light source device 5 will be described, but the lighting method can be appropriately changed according to the type of the imaging unit 20, and for example, a surface-sequential lighting method may be used. Further, the light source device 5 may also supply special light for white light. As the special light, for example, narrow band light capable of narrow band imaging (NBI), infrared light, violet light, orange light, and the like may be supplied.

Configuration of Imaging Unit

Figure 2:
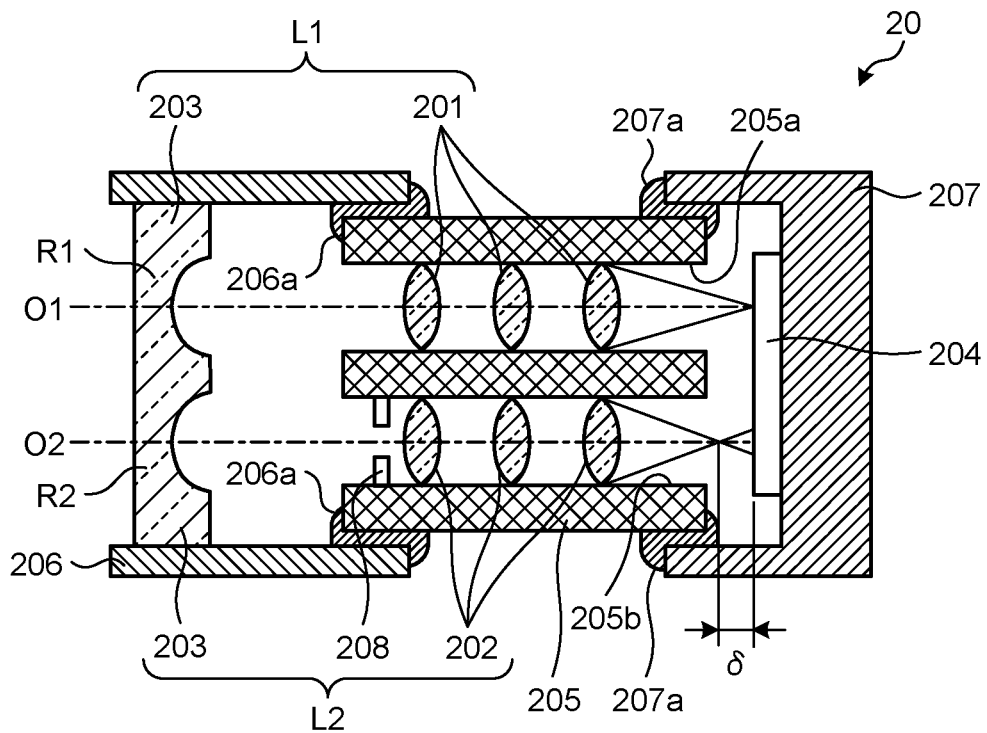
FIG. 2 is a diagram schematically illustrating a cross section of one imaging unit according to one embodiment of the present disclosure.

Next, a configuration of the imaging unit 20 will be described. FIG. 2 is a diagram schematically illustrating a cross section of the imaging unit 20.

The imaging unit 20 illustrated in FIG. 2 includes a first lens group 201, a second lens group 202, an objective lens group 203, an image sensor 204, a first holding frame 205, a second holding frame 206, a third holding frame 207, and a diaphragm 208.

The first lens group 201 forms an image of object light guided from the objective lens group 203 on a light receiving surface of the image sensor 204 as a first optical image. The first lens group 201 is configured by using a plurality of lenses.

The second lens group 202 forms a pair with the first lens group 201, and forms an image of the object light guided from the objective lens group 203 on the light receiving surface of the image sensor 204 as a second optical image. The second lens group 202 is configured by using a plurality of lenses.

The objective lens group 203 has a first region R1 that guides the object light to the first lens group 201, and a second region R2 that guides the object light to the second lens group 202. The objective lens group 203 is configured by using a plurality of lenses. The following description will be given while an optical system (left optical system) composed of the objective lens group 203 and the first lens group 201 is referred to as a first optical system L1, and an optical system (right optical system) composed of the objective lens group 203 and the second lens group 202 is referred to as a second optical system L2. Further, the first optical system L1 and the second optical system L2 function as a stereo optical system having a parallax.

The image sensor 204 generates an imaging signal by receiving the first optical image formed by the first lens group 201 and the second optical image formed by the second lens group 202. The image sensor 204 is configured by using a single charge coupled device (CCD), a single complementary metal oxide semiconductor (CMOS), or the like. The image sensor 204 is not limited to a single one, and may be configured by using a plurality of plates that receives each of the first optical image and the second optical image.

The first holding frame 205 has a tubular shape. The first holding frame 205 has a first holding hole 205a in which the first lens group 201 is held and a second holding hole 205b in which the second lens group 202 is held. The first holding hole 205a and the second holding hole 205b are integrally formed. The first holding hole 205a and the second holding hole 205b internally hold the first lens group 201 and the second lens group 202, respectively, so that an optical axis O1 of the first lens group 201 and an optical axis O2 of the second lens group 202 have predetermined parallaxes.

The second holding frame 206 has a tubular shape and holds the objective lens group 203. The second holding frame 206 is positioned and fixed with respect to the first holding frame 205 by being adhered with an adhesive 206a or the like to an outer peripheral surface of the first holding frame 205 on a distal end side (one end side) of the first holding frame 205 in a state where an inner peripheral surface of the second holding frame 206 is fitted to the outer peripheral surface of the first holding frame 205 on the distal end side of the first holding frame 205. As a fixing method, in addition to the adhesive, for example, a spiral groove or a female screw may be provided on an outer peripheral side of the first holding frame 205, and a male screw may be provided on an inner peripheral side of the second holding frame 206 for fixation.

The third holding frame 207 holds the image sensor 204. The third holding frame 207 has a tubular shape, and is positioned and fixed with respect to the first holding frame 205 by being adhered with an adhesive 207a or the like to the outer peripheral surface of the first holding frame 205 on a proximal end side (another end side) of the first holding frame 205 in a state where an inner peripheral surface of the third holding frame 207 is fitted to the outer peripheral surface of the first holding frame 205 on the proximal end side of the first holding frame 205. As a fixing method, in addition to the adhesive, for example, a spiral groove or a female screw may be provided on the outer peripheral side of the first holding frame 205, and a male screw may be provided on an inner peripheral side of the third holding frame 207 for fixation.

The diaphragm 208 is arranged on an optical path of the second optical system L2, and changes an F-number (F value) of the second optical system L2 by limiting light incident on the second lens group 202. The diaphragm 208 is arranged on the optical path of the second optical system L2. Specifically, the diaphragm 208 is arranged between the objective lens group 203 and the second lens group 202 on the optical path of the second optical system L2. The location of the diaphragm 208 can be changed as appropriate. For example, the diaphragm 208 can be arranged between the second lens group 202 and the image sensor 204, or a distal end side of the objective lens group 203, or between the lenses of the second lens group 202.

In the imaging unit 20 configured in this way, an F-number (F value) of the first optical system L1 (primary optical system) is larger than the F-number (F value) of the second optical system L2 (secondary optical system). Specifically, in the second optical system L2, since the diaphragm 208 is provided between the objective lens group 203 and the second lens group 202, the F-number (F value) of the second optical system L2 is smaller than the F-number (F value) of the first optical system L1.

Figure 3:
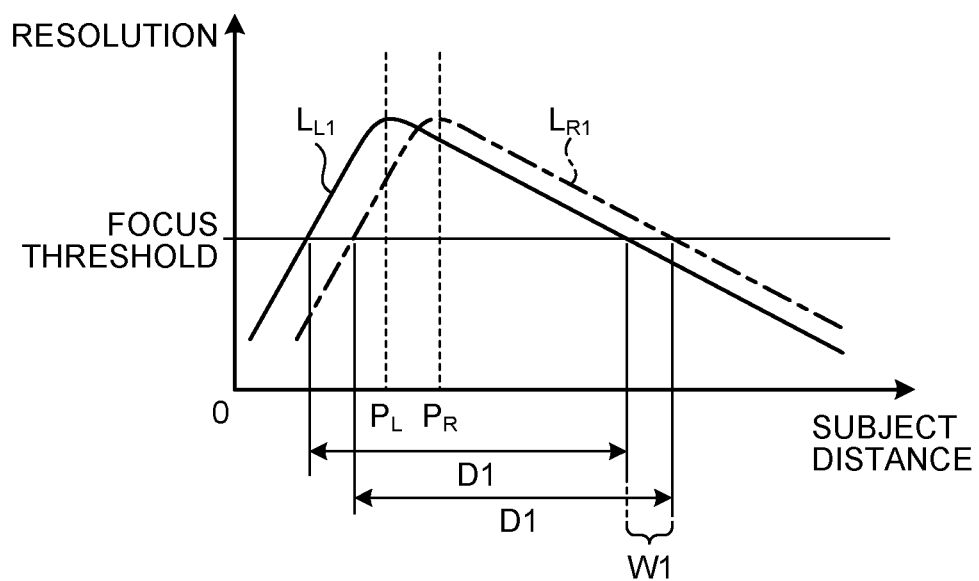
FIG. 3 is a graph illustrating a relationship between resolution and subject distance when F-numbers of a first optical system and a second optical system are set to a same value according to one embodiment of the present disclosure.
Figure 4:
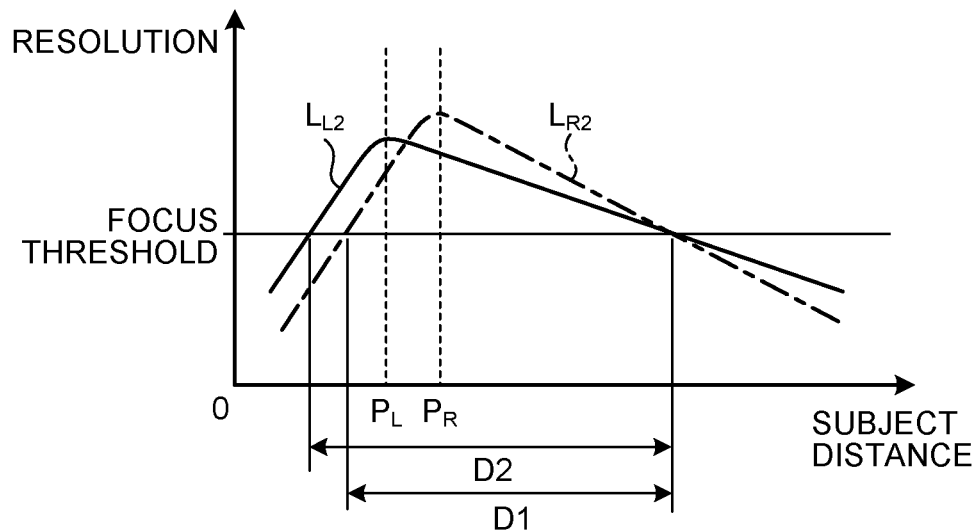
FIG. 4 is a graph illustrating a relationship between the resolution and the subject distance when the F-number of the first optical system is set to a value larger than the F-number of the second optical system according to one embodiment of the present disclosure.

FIG. 3 is a diagram illustrating a relationship between resolution and subject distance when the F-numbers of the first optical system L1 and the second optical system L2 are set to a same value. FIG. 4 is a diagram illustrating the relationship between the resolution and the subject distance when the F-number of the first optical system L1 is set to a value larger than the F-number of the second optical system L2. In FIGS. 3 and 4, the horizontal axis represents the subject distance and the vertical axis represents the resolution. Further, curves $L_{L1}$ and $L_{L2}$ of FIGS. 3 and 4 represent characteristics of the first lens group 201, and curves $L_{R1}$ and $L_{R2}$ of FIGS. 3 and 4 represent characteristics of the second lens group 202. Further, in FIGS. 3 and 4, a threshold LT represents a focus threshold.

As shown in FIG. 3, in a conventional configuration (hereinafter referred to as "configuration 1"), since the F-numbers of the first optical system L1 and the second optical system L2 are the same, a lens frame of either the first optical system L1 or the second optical system L2 is adjusted. As a result, in configuration 1, since a depth of field D1 of each of the first optical system L1 and the second optical system L2 is the same, each of the first optical system L1 and the second optical system L2 can be adjusted to the same focus position, but focusing adjustment work becomes complicated. Further, even in a configuration (hereinafter referred to as "configuration 2") in which only a part of lenses of either the first optical system L1 or the second optical system L2 can be adjusted to be in focus of the other optical system, the lens frame becomes complicated and the focusing adjustment work becomes complicated. Specifically, in the conventional configuration 2, after the focus is adjusted between the first optical system L1 and the second optical system L2 (adjustment step 1), a part of lenses that form the second optical system L2 is moved in a direction of the optical axis O2 so as to adjust the focus (adjustment step 2). That is, in the conventional configuration 2, two adjustment steps have to be performed, and in addition, a structure for moving only a part of the lenses of the second optical system L2 needs to be separately provided, and thus the frame mechanism becomes complicated.

On the other hand, as shown in FIG. 4, in the imaging unit 20, the F-number (F value) of the first optical system L1 is set larger than the F-number (F value) of the second optical system L2. Specifically, as shown in FIG. 4, in the imaging unit 20, by setting the F-number of the first optical system L1 larger than the F-number of the second optical system L2, a depth of field D2 with respect to a subject PR is magnified so as to include the depth of field D1 of the second optical system L2. That is, an in-focus range of the second optical system L2 is adjusted to an in-focus range of the first optical system L1. As a result, the focus adjustment of the first optical system L1 and the second optical system L2 can be performed with a simple configuration without providing a special focus adjustment member. Further, in the imaging unit 20, configurations of the first holding frame 205 to the third holding frame 207 can be simplified as compared with the conventional configuration 2 described above, and focus of the first optical system L1 and the second optical system L2 can be adjusted with only single adjustment work. Furthermore, as a feature of 3D composite images, when two images are combined, human eyes are strongly affected by a high-resolution image on one side, and as a result, the F value on one side may be increased to decrease the resolution. A 3D image obtained by utilizing this effect gives a high-definition impression.

Configuration of Processing Device

Figure 5:
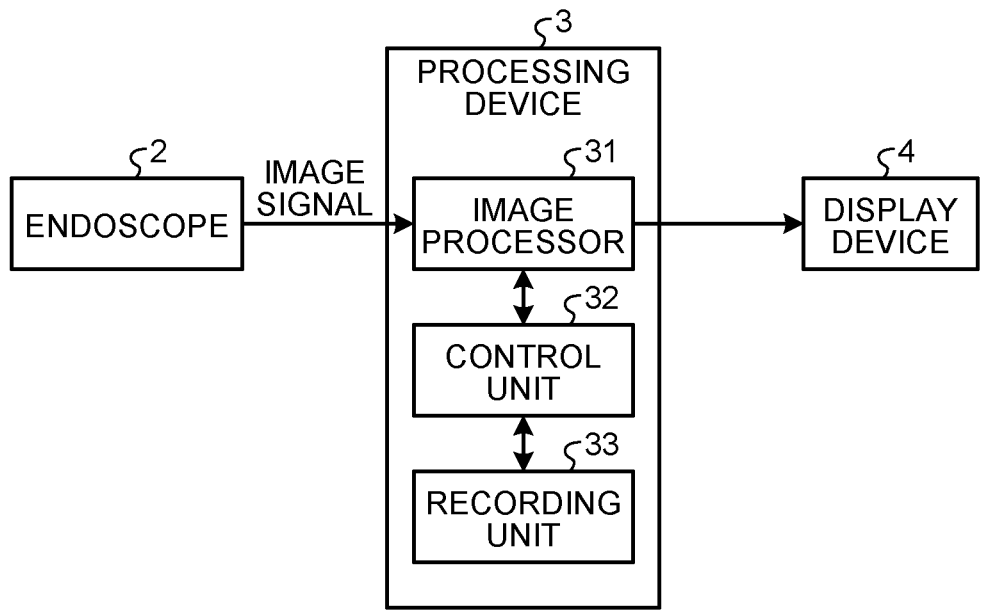
FIG. 5 is a block diagram illustrating a functional configuration of a processing device according to one embodiment of the present disclosure.

Next, a configuration of the processing device 3 will be described. FIG. 5 is a block diagram illustrating a functional configuration of the processing device 3.

The processing device 3 illustrated in FIG. 5 includes an image processor 31, a control unit 32, and a recording unit 33.

The image processor 31 performs various processing on an image signal input from the endoscope 2 and outputs the image signal to the display device 4. The image processor 31 is configured by using, for example, a graphics processing unit (GPU), an application specific integrated circuit (ASIC), a digital signal processing (DSP), a field programmable gate array (FPGA), or the like.

The control unit 32 controls each unit of the endoscope system 1. The control unit 32 is configured by using a CPU (Central Processing Unit) or the like.

The recording unit 33 records various data related to the endoscope system 1 and a program to be executed. The recording unit 33 is configured by using a volatile memory, a non-volatile memory, a memory card, or the like.

Processing of Processing Device

Next, an outline of processing executed by the processing device 3 will be described. FIG. 6 is a flowchart illustrating the outline of processing executed by the processing device 3. Note that even when performing 3D observation, the endoscope 2 basically records one of a 2D image, for example, a first image generated by the first optical system L1 (hereinafter referred to as "sub-image") and a second image generated by the second optical system L2 (hereinafter referred to as "main image"). Preferably, the endoscope 2 records the main image. Currently, super-resolution technology is known for the endoscope 2, but since in most cases of this technology, the number of imaging pixels of the image sensor 204 is smaller than the number of display pixels of the display device 4, there is a difference between the number of display pixels and the number of imaging pixels. Therefore, interpolation processing and edge enhancement processing are performed in the processing device 3 to which the endoscope 2 is connected so as to reproduce a vivid image. Moreover, at present, learning-type super-resolution technology is known for the endoscope 2, but since the subject moves, unlike still life, it is difficult to obtain teacher data. In addition, since real-time performance is insufficient, there is also a problem that this type lacks affinity with automatic detection/diagnosis such as computer-aided detection (CADe) and computer-aided diagnosis (CADx). Further, at present, in the endoscope 2, the processing device 3 performs edge enhancement, but there is an influence on information adjacent to an edge, for example, not only dark gray becoming black, but also light gray changing to white. Therefore, in the following, the processing of the processing device 3 executed by the endoscope system 1 during 2D image observation or 2D image storage instead of 3D image observation will be described.

As shown in FIG. 6, first, the image processor 31 acquires a main image and a sub-image from an image signal generated by the image sensor 204 of the endoscope 2 (step S101).

Subsequently, the image processor 31 executes image adjustment processing of the sub-image with respect to the main image (step S102). Specifically, the image processor 31 executes offset processing for calculating a parallax value which is an amount of deviation from a predetermined position, for example, a center, of the main image to a center of the sub-image, magnification adjustment processing for adjusting magnification of the main image and the sub-image, distortion adjustment processing for adjusting distortion of the main image and the sub-image, rotation processing for adjusting horizontality and verticality of the main image and the sub-image, and the like.

After that, based on the parallax value calculated by the offset processing, the image processor 31 calculates a difference value between luminance information of each pixel of the main image and luminance information of each pixel of the sub-image (step S103). Specifically, the image processor 31 aligns positions of the pixels of the main image and the sub-images based on a parallax amount (deviation amount) calculated by the offset processing, and then calculates the difference value between the luminance information (pixel value) of each pixel of the main image and the luminance information of each pixel of the sub-image.

Subsequently, the image processor 31 adds the difference value calculated in step S103 to a pixel value of each pixel of the main image (step S104), and records the value in the recording unit 33 (step S105). After step S105, the image processor 31 ends the processing. The image processor 31 simply adds the difference value calculated in step S103 to the pixel value of each pixel of the main image, but the calculation is not limited to this, and an absolute value of the difference value may be added to the pixel value of each pixel of the main image. As a result, according to one embodiment, by simultaneously acquiring two images, which are the main image and the sub-image, using one image sensor 204, enhancement processing can be performed by a simple calculation, and thus the real-time performance can be improved. According to one embodiment, since the enhancement processing can be performed by a simple calculation, a scale of a circuit constituting the image processor 31 can be reduced. Further, according to one embodiment, the F-number (F value) of the second optical system L2 is smaller than the F-number (F value) of the first optical system L1. Therefore, since the first optical system L1 (secondary optical system) has a deep depth of field, the 2D image saved by the enhancement processing has an enlarged depth of field. Furthermore, according to one embodiment, since it is possible to improve contrast and a sense of resolution, and it is also possible to prevent influence on peripheral pixels caused by the sub-image, an enhanced image without a feeling of incompatibility can be provided.

According to one embodiment of the present disclosure described above, the F-number (F value) of the first optical system L1 is larger than the F-number (F value) of the second optical system L2 so that focus adjustment of the first optical system L1 and the second optical system L2 can be performed with a simple configuration.

According to one embodiment of the present disclosure, the F-number (F value) of the first optical system L1 is larger than the F-number (F value) of the second optical system L2, but the configuration is not limited to this, and the F-number (F value) of the second optical system L2 may be larger than the F-number (F value) of the first optical system L1. That is, by setting the F-number of one of the two optical systems larger than the F-number of the other, the focus adjustment of the two optical systems can be performed with a simple configuration.

In one embodiment of the present disclosure, either the first optical system L1 or the second optical system L2 may be provided with a filter, on the optical path, that cuts light in a part of a wavelength band, or lenses may be coated. Here, a filter may be inserted or coating may be applied for cutting, as light in a part of the wavelength band, a wavelength band of photodynamic therapy (PDT) (600 to 800 nm), a wavelength band of a tunable yttrium aluminum garnet (YAG) laser (for example, 1064 nm), a wavelength band of a laser diode (LD) laser (650 to 905 nm), etc. This makes it possible to observe a 2D image according to each mode.

Further, in one embodiment of the present disclosure, an actuator for switching a focal position may be provided in either the first optical system L1 or the second optical system L2, or an actuator for switching focal length may be provided. As a result, the focal position and the focal length can be changed according to an observation target.

Further, in one embodiment of the present disclosure, a switching mechanism such as a diaphragm mechanism, a filter mechanism, a lens mechanism, etc. that has a fan shape and can move in a radial direction around an axial direction of the endoscope may be attached to the distal end portion 101 of the endoscope 2. In this case, the switching mechanism is inserted into the optical path of the first optical system L1 or the second optical system L2 by supplying an electric current to an actuator such as a coil that drives the endoscope 2 in the radial direction. As a result, it is possible to perform observation according to an observation target and a treatment target, and effectively utilize a dead space generated in a direction perpendicular to a line connecting the optical axes of the first optical system L1 and the second optical system L2, and thus miniaturization can be realized.

Further, in one embodiment of the present disclosure, instead of a color filter of Bayer arrangement arranged on the light receiving surface of the image sensor 204 that receives an optical image of at least one of the first optical system L1 and the second optical system L2, for example, a complementary color filter composed of a B filter (blue filter), a Cy filter (cyan filter), a Ye filter (yellow filter), and an Mg filter (magenta filter) may be arranged.

Further, in one embodiment of the present disclosure, a frame rate of a pixel region of the light receiving surface of the image sensor 204 that receives an optical image of at least one of the first optical system L1 and the second optical system L2 may be set higher (for example, 120 fps) than the frame rate (for example, 60 fps) of a pixel region of the other one. By increasing the frame rate of the pixel region recorded as a 2D image, it is possible to prevent subject blurring. In addition, a processing circuit can be miniaturized as compared with a case where the pixel regions of both the first optical system L1 and the second optical system L2 are accelerated. Further, since it is possible to capture an image at a high frame rate in a surface-sequential light emission mode in which a type of illumination light is switched at high speed, it is possible to prevent subject blurring and color shift.

In addition, various embodiments can be formed by appropriately combining a plurality of components disclosed in the endoscope system according to one embodiment of the present disclosure. For example, some components may be deleted from all the components described in the endoscope system according to one embodiment of the present disclosure described above. Further, the components described in the endoscope system according to one embodiment of the present disclosure described above may be appropriately combined.

Further, in the endoscope system according to one embodiment of the present disclosure, the above-mentioned "unit" can be read as "means", "circuit", and the like. For example, the control unit can be read as a control means or a control circuit.

Further, a program to be executed by the endoscope system according to one embodiment of the present disclosure is recorded and provided in a computer-readable recording medium such as a compact disk read only memory (CD-ROM), a flexible disk (FD), a compact disc recordable (CD-R), a digital versatile disk (DVD), a universal series bus (USB) medium, or a flash memory as file data in an installable format or an executable format.

Further, the program to be executed by the endoscope system according to one embodiment of the present disclosure may be stored on a computer connected to a network such as the Internet and provided by downloading via the network.

In the description of a timing chart in the present specification, the context of processing between steps is clarified by using expressions such as "first", "after", and "subsequently", but an order of processing required for carrying out the disclosure is not uniquely defined by those expressions. That is, the order of processing in the timing chart described in the present specification can be changed within a consistent range.

According to the present disclosure, there is an effect that focus adjustment of two optical systems can be easily performed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit comprising:
   a first lens group configured to form a first optical image;
   a second lens group configured to form a pair with the first lens group and form a second optical image;
   an objective lens group having a first region that guides object light to the first lens group and a second region that guides object light to the second lens group;
   a single image sensor configured to generate an image signal by receiving the first optical image and the second optical image;
   a first holding frame having a first holding hole in which the first lens group is held and a second holding hole in which the second lens group is held;
   a second holding frame configured to hold the objective lens group, the second holding frame being positioned and fixed with respect to the first holding frame by being adhered to a distal end side of the first holding frame in a state where the second holding frame is fitted to the distal end side of the first holding frame; and
   a third holding frame configured to hold the image sensor, the third holding frame being positioned and fixed with respect to the first holding frame by being adhered to a proximal end side of the first holding frame in a state where the third holding frame is fitted to the proximal end side of the first holding frame on an inner peripheral surface of the third holding frame, wherein a depth of field of a first optical system formed of the objective lens group and the first lens group is set so as to entirely include a depth of field of a second optical system formed of the objective lens group and the second lens group and to be deeper than the depth of field of the second optical system.

2. The imaging unit according to claim 1, wherein the second optical system further includes a diaphragm on an optical path of the second optical system, and the diaphragm is configured to limit light incident on the second lens group such that the depth of field of the first optical system is set so as to entirely include the depth of field of the second optical system and to be deeper than the depth of field of the second optical system.

3. An endoscope comprising:

an insertion portion to be inserted into a subject;

an imaging unit provided on a distal end side of the insertion portion and generating an image signal by capturing an image of the subject; and a proximal end portion provided on a proximal end side of the insertion portion and detachably connected to a processor configured to perform image processing on the image signal, wherein the imaging unit includes a first lens group configured to form a first optical image;

a second lens group configured to form a pair with the first lens group and form a second optical image;

an objective lens group having a first region that guides object light to the first lens group and a second region that guides object light to the second lens group;

a single image sensor configured to generate an image signal by receiving the first optical image and the second optical image;

a first holding frame having a first holding hole in which the first lens group is held and a second holding hole in which the second lens group is held;

a second holding frame configured to hold the objective lens group, the second holding frame being positioned and fixed with respect to the first holding frame by being adhered to a distal end side of the first holding frame in a state where the second holding frame is fitted to the distal end side of the first holding frame; and a third holding frame configured to hold the image sensor, the third holding frame being positioned and fixed with respect to the first holding frame by being adhered to a proximal end side of the first holding frame in a state where the third holding frame is fitted to the proximal end side of the first holding frame on an inner peripheral surface of the third holding frame, wherein a depth of field of a first optical system formed of the objective lens group and the first lens group is set so as to entirely include a depth of field of a second optical system formed of the objective lens group and the second lens group and to be deeper than the depth of field of the second optical system.

4. An endoscope system comprising:

the endoscope according to claim 3; and a processor configured to acquire, based on the image signal, a first image generated by the first optical system and a second image generated by the second optical system, calculate a parallax value that is an amount of deviation of a predetermined position of each of the second image and the first image, calculate, based on the parallax value, a difference value between luminance information of each pixel of the second image and luminance information of each pixel of the first image, and add the difference value to a pixel value of each pixel of the second image.

* * * * *